United States Patent
Vetter et al.

(10) Patent No.: US 7,635,340 B2
(45) Date of Patent: Dec. 22, 2009

(54) METHODS AND DEVICES FOR REMOVING TISSUE FROM A PATIENT

(75) Inventors: James W. Vetter, Portola Valley, CA (US); Ary S. Chernomorsky, Walnut Creek, CA (US); Christopher Daniel, Palo Alto, CA (US); Mark J. Clifford, Los Altos, CA (US); Scott C. Anderson, Sunnyvale, CA (US)

(73) Assignee: Rubicor Medical, Inc., Redwood City, CA (US)

( * ) Notice: Subject to any disclaimer, the term of this patent is extended or adjusted under 35 U.S.C. 154(b) by 0 days.

(21) Appl. No.: 11/099,985

(22) Filed: Apr. 5, 2005

(65) Prior Publication Data

US 2006/0224084 A1    Oct. 5, 2006

(51) Int. Cl.
*A61B 10/00*    (2006.01)
*A61B 17/32*    (2006.01)
*A61B 17/14*    (2006.01)
*A61B 17/34*    (2006.01)

(52) U.S. Cl. .................. 600/564; 600/562; 600/567; 606/167; 606/170; 606/174; 606/180; 606/184; 606/185

(58) Field of Classification Search ............... 600/562, 600/564, 567; 606/167, 170, 174, 180, 184, 606/185
See application file for complete search history.

(56) References Cited

U.S. PATENT DOCUMENTS

| | | | | |
|---|---|---|---|---|
| 4,651,752 A * | 3/1987 | Fuerst | ............ | 600/567 |
| 4,926,877 A * | 5/1990 | Bookwalter | ............ | 600/567 |
| 5,074,311 A * | 12/1991 | Hasson | ............ | 600/567 |
| 5,267,572 A * | 12/1993 | Bucalo | ............ | 600/567 |
| 5,324,300 A * | 6/1994 | Elias et al. | ............ | 606/180 |
| 5,462,062 A * | 10/1995 | Rubinstein et al. | ............ | 600/567 |
| 5,810,806 A * | 9/1998 | Ritchart et al. | ............ | 606/45 |
| 5,817,034 A * | 10/1998 | Milliman et al. | ............ | 600/566 |
| 5,857,982 A * | 1/1999 | Milliman et al. | ............ | 600/567 |
| 5,910,121 A * | 6/1999 | Paolo et al. | ............ | 600/562 |
| 5,980,469 A * | 11/1999 | Burbank et al. | ............ | 600/567 |
| 6,036,657 A * | 3/2000 | Milliman et al. | ............ | 600/564 |
| 6,068,603 A * | 5/2000 | Suzuki | ............ | 600/565 |
| 6,142,957 A * | 11/2000 | Diamond et al. | ............ | 600/567 |
| 6,471,700 B1 * | 10/2002 | Burbank et al. | ............ | 606/45 |
| 6,638,234 B2 * | 10/2003 | Burbank et al. | ............ | 600/564 |
| 7,094,233 B2 * | 8/2006 | Desinger | ............ | 606/45 |
| 2001/0007925 A1 * | 7/2001 | Ritchart et al. | ............ | 600/567 |
| 2002/0016555 A1 * | 2/2002 | Ritchart et al. | ............ | 600/567 |
| 2002/0120212 A1 * | 8/2002 | Ritchart et al. | ............ | 600/567 |

* cited by examiner

*Primary Examiner*—Max Hindenburg
*Assistant Examiner*—Jeffrey G Hoekstra
(74) *Attorney, Agent, or Firm*—Jens E. Hoekendijk

(57) ABSTRACT

The present invention is directed to tissue removal devices and methods. A tubular element having an open distal end is advanced into tissue so that tissue enters the tubular element. The tissue which entered the tubular element is cut to separate the tissue from the surrounding tissue. The tissue is then transported proximally by the cutting element or a separate transport element.

10 Claims, 15 Drawing Sheets

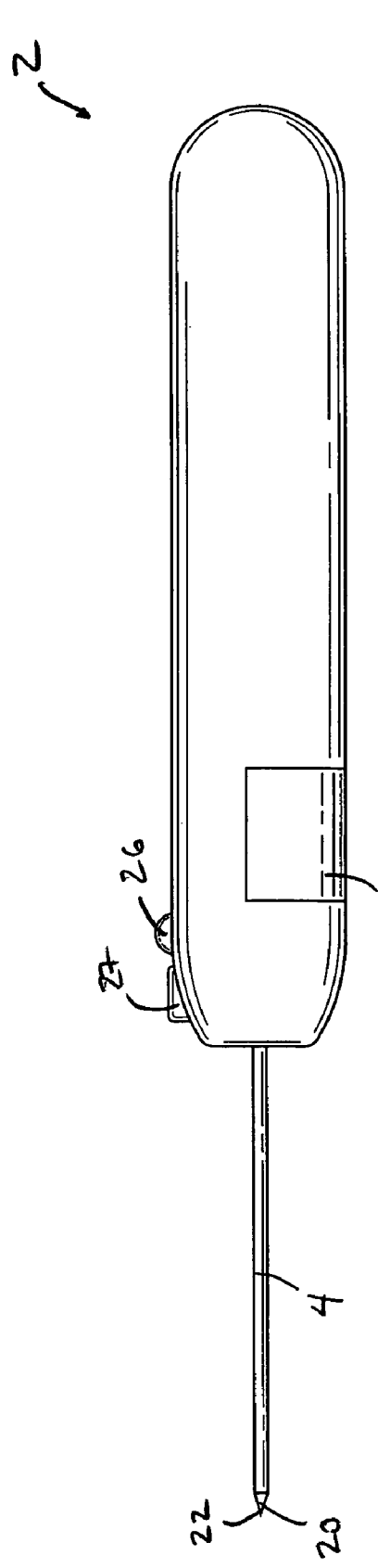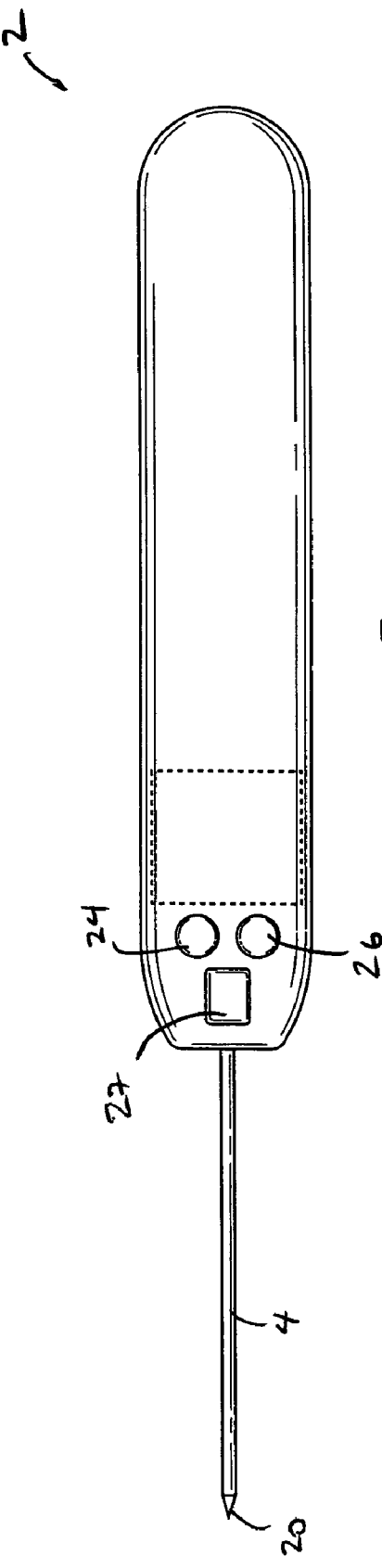

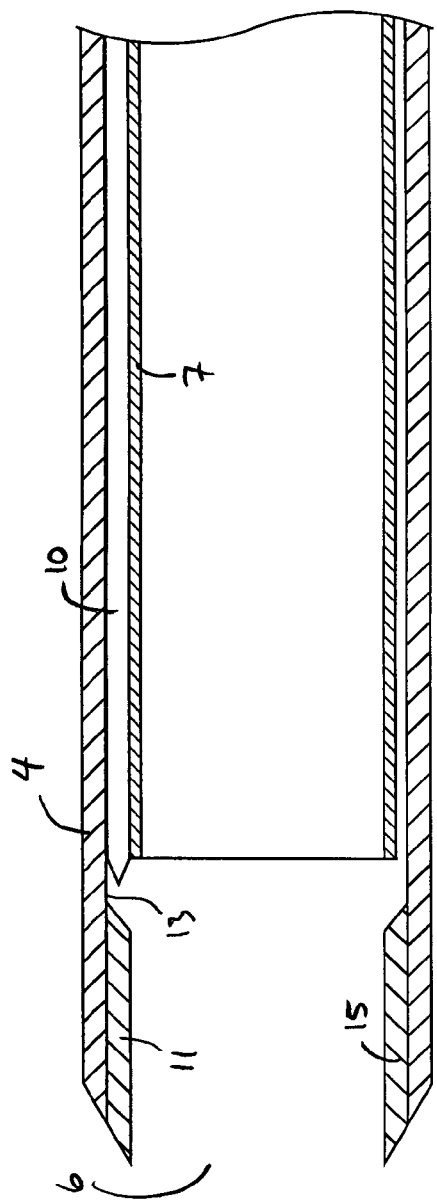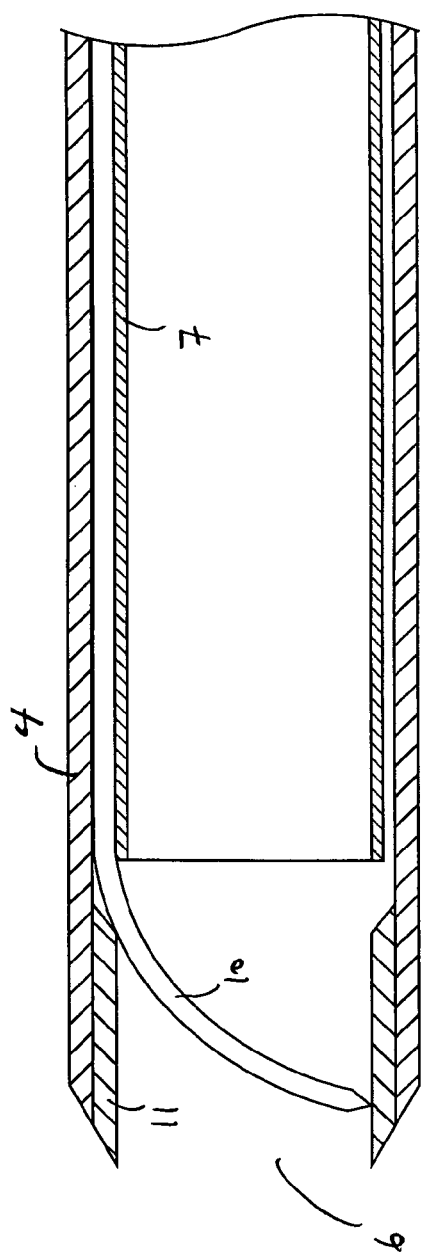

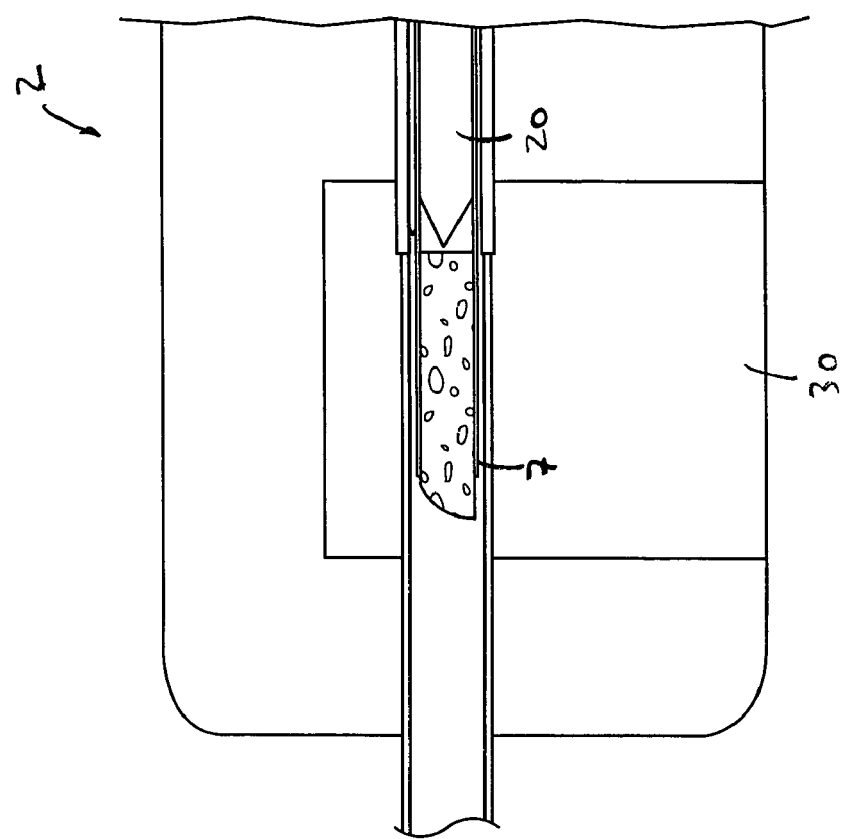
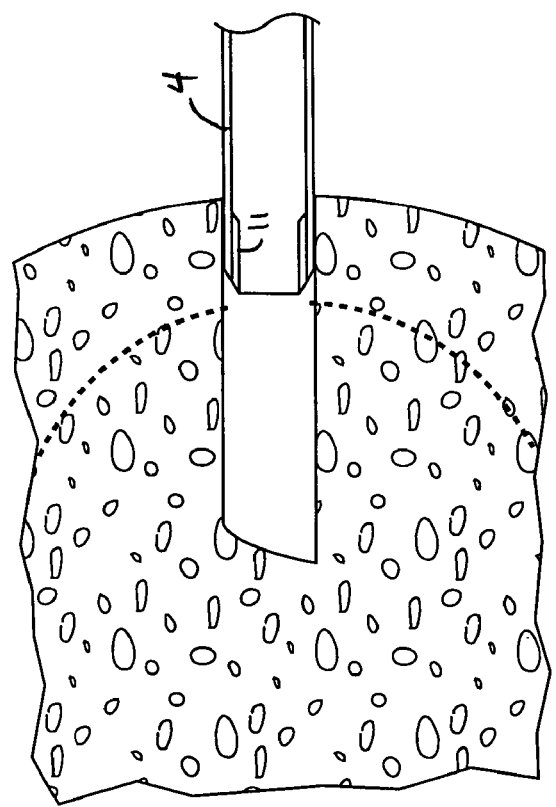
FIG. 10

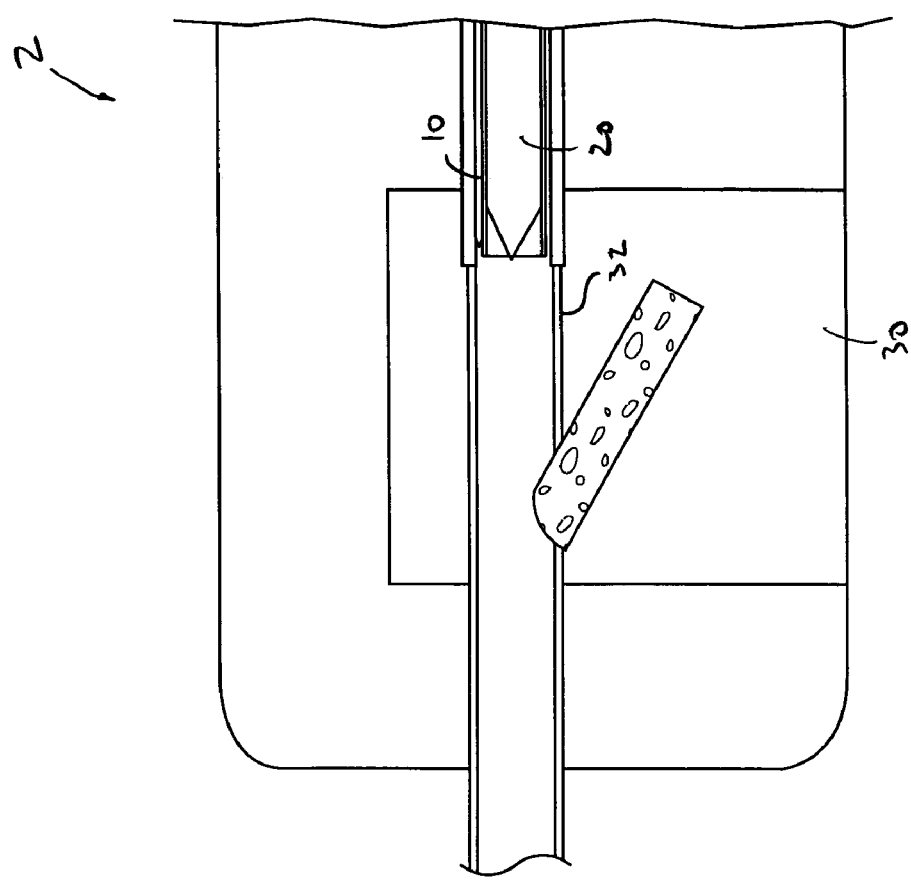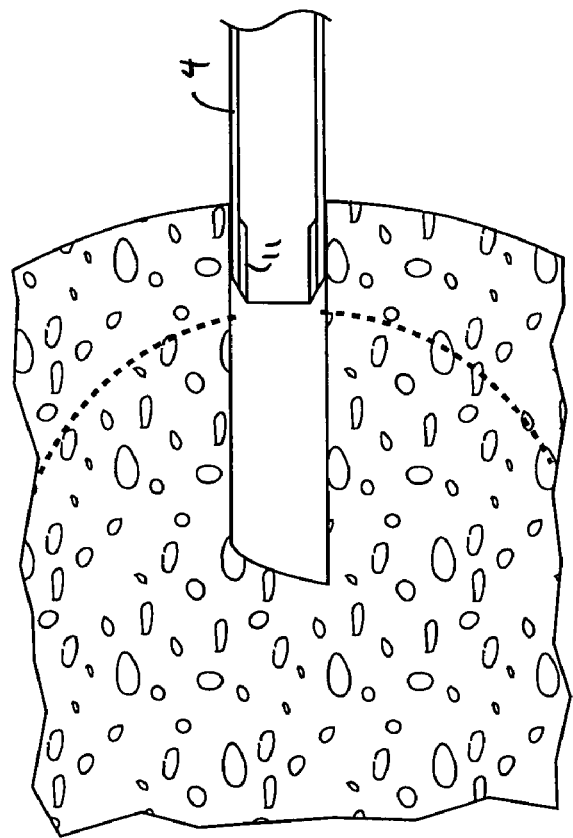
FIG. 11

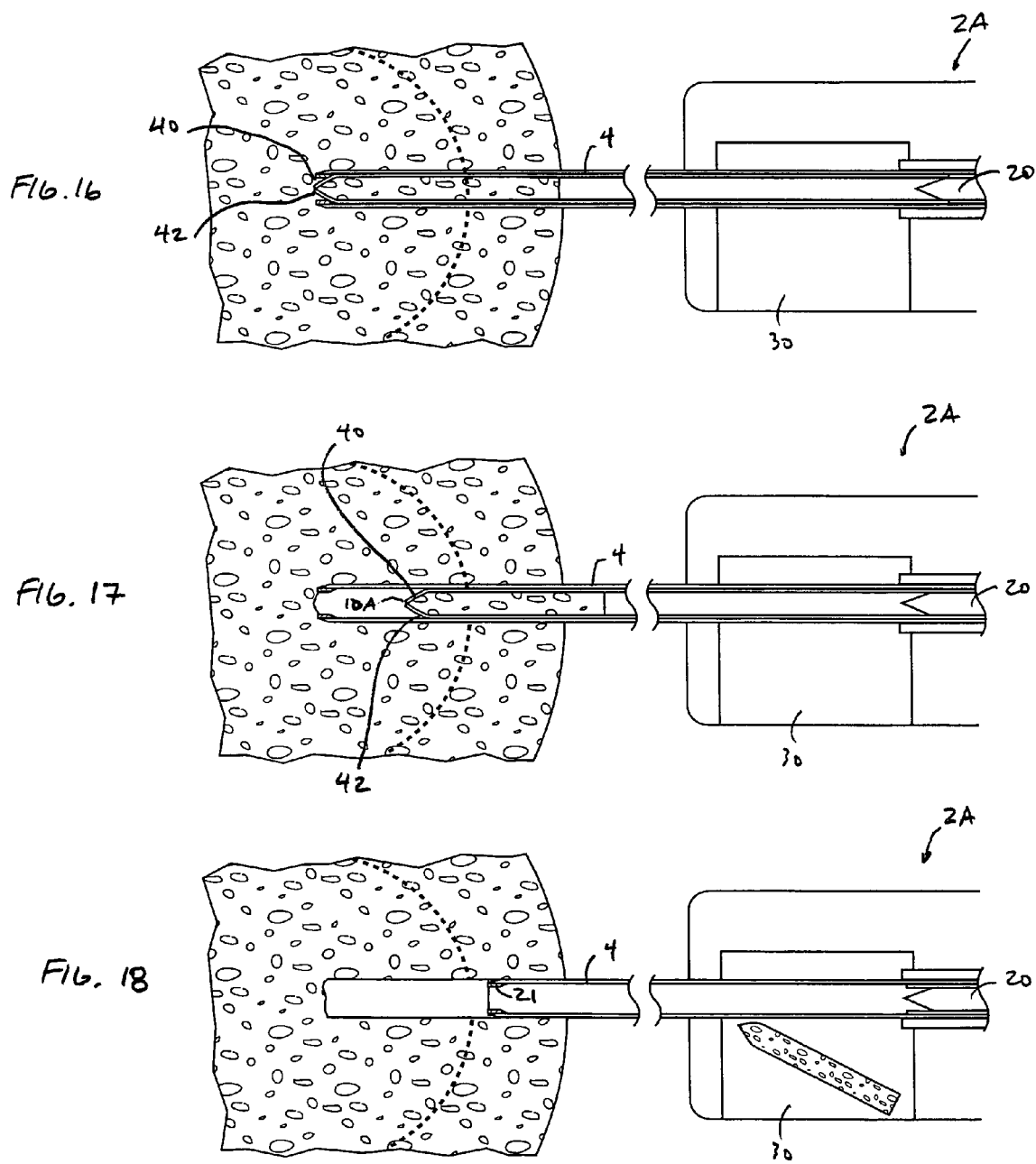

METHODS AND DEVICES FOR REMOVING TISSUE FROM A PATIENT

BACKGROUND

The present invention is directed to tissue removing devices and methods. The invention may be used to remove tissue from any part of the body and is particularly useful in removing tissue from the breast. Of course, the invention may be used in any other part of the body and use in the breast is merely exemplary.

SUMMARY

In a first aspect of the present invention, a tissue removal device is provided which has a tubular element, a transport element and a cutting element. The tubular element has an open distal end. The transport element and the cutting element are positioned at least partially within the tubular element and are movable within the tubular element. The device is introduced into a patient and the tubular element is advanced so that tissue enters the tubular element through the open end. The cutting element is then used to cut or part-off the tissue which has entered the tubular element and the transport element is used to transport the tissue proximally to a tissue chamber.

The transport element may take many forms. In one embodiment, the transport element has an open end positioned proximal to the open end of the tubular element so that tissue enters the open end of the transport element when the tubular element is advanced into tissue. The transport element may also pierce the tissue being removed from the patient. Furthermore, the transport element may have a deployable anchor which secures the tissue to the transport element. The anchor may take any suitable shape such as deployable barbs, wires or an inflatable balloon.

In another aspect of the present invention, the device may include a cutting element which parts off the tissue which enters the tubular element and also transports the tissue to the tissue chamber. The cutting element may have a first part and a second part which move toward one another to a cutting position when cutting the tissue within the tubular element. The cutting element may be plastically deformed when moving to a cutting position.

These and other aspects of the present invention shall become apparent from the following description, drawings and claims.

DESCRIPTION OF DRAWINGS

FIG. 1 shows a tissue removing device in accordance with the present invention.

FIG. 2 shows another view of the device of FIG. 1.

FIG. 3 is a cross-sectional view of a distal end of the tissue removal device with a cutting element in a stored position.

FIG. 4 is a cross-sectional view showing the cutting element in a cutting position.

FIG. 10 shows the tissue positioned over a tissue chamber and contacting a distal end of the introducer.

FIG. 11 shows the tissue falling into the tissue chamber.

FIG. 16 shows the cutting element in a cutting position.

FIG. 17 shows the cutting element moving the tissue proximally toward the tissue chamber.

FIG. 18 shows the tissue being released into the tissue chamber by the cutting element.

DESCRIPTION OF THE PREFERRED EMBODIMENTS

Figure 5:
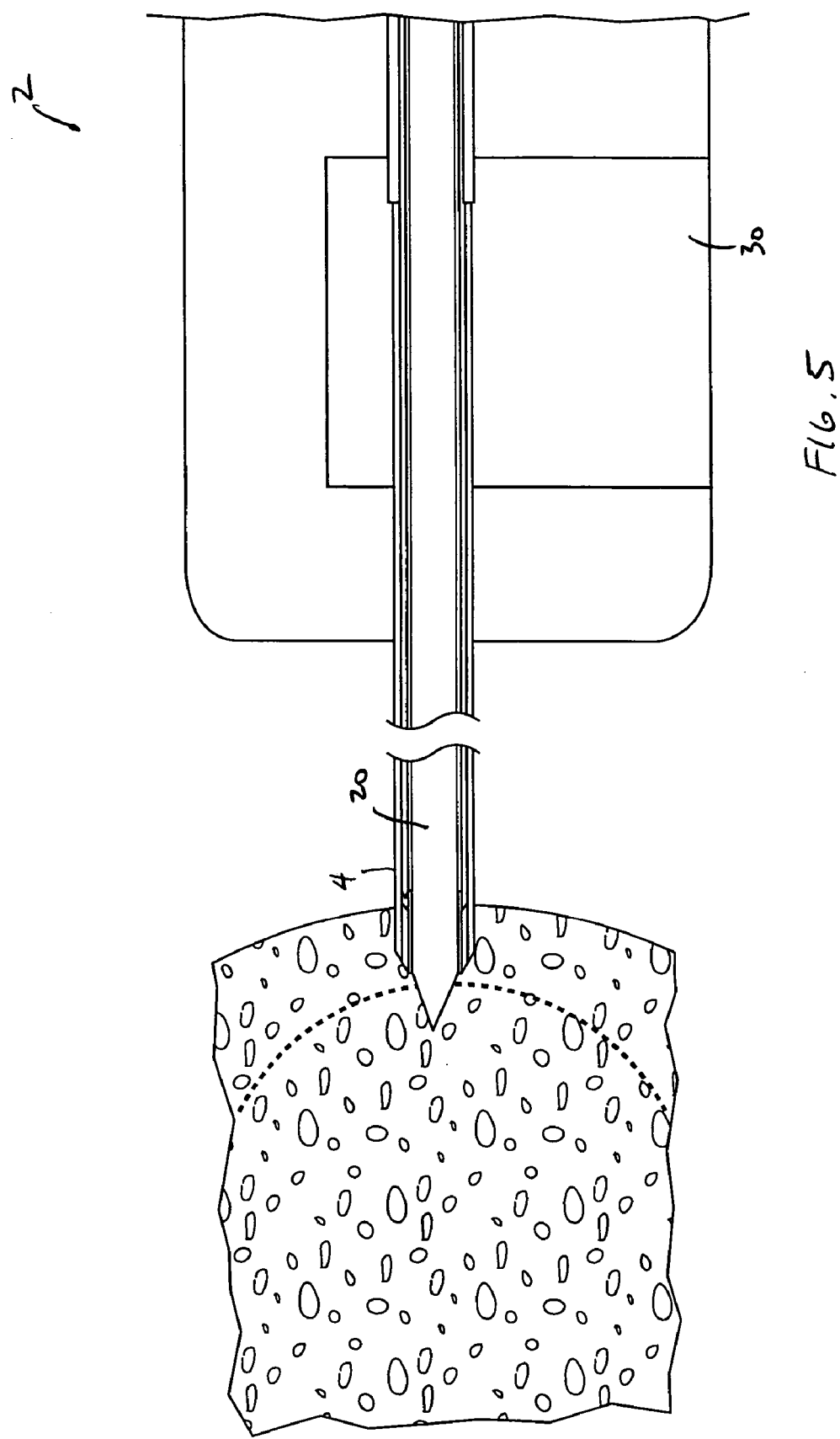
FIG. 5 shows the device being introduced into tissue.

Referring to FIGS. 1-11, a tissue removing device 2 according to the present invention is shown. The devices and methods described herein may be used to remove tissue from any location in the body and an example of such a use is removal of tissue from the breast as described below. The tissue removal device 2 has a tubular element 4 which is advanced into tissue so that tissue is received through an open end 6 of the tubular element 4. A transport element 7 is positioned within the tubular element 4 and is used to transport tissue back to a tissue sample chamber 30 as described below.

The distal end of the tubular element 4 is beveled to form a sharp tip 11 but may take any other suitable configuration which penetrates tissue. The tubular element 4 may also be rotated when driven into the tissue. The tubular element 4 may be made of any suitable material such as stainless steel. The device 2 may also include an introducer 20 positioned in the tubular element 4 during introduction. The introducer 20 may have a sharp tip 22 which penetrates the tissue during introduction of the device 2 as shown in FIG. 5. The device 2 may also be introduced through a sheath, trocar or cannula (not shown) which penetrates the tissue rather than using the device 2 itself to penetrate the tissue.

Although the present invention may be used to collect tissue of any size, the invention is particularly useful in removing relatively small quantities of tissue such as required in breast biopsies. When used for this purpose, the inner diameter of the device 2 may be less than 5 mm or even less than 3.5 mm. The present invention provides the ability to obtain small, cylindrical tissue samples which are relatively undisturbed compared to many prior art solutions. The tubular element 4 may be driven forward a distance of 15-25 mm which may be selected by the user.

The tissue removal device 2 also has a cutting element 10 which is used to cut or "part off" tissue which has entered the tubular element 4 from the surrounding tissue. The cutting element 10 is stored between the tubular element 4 and the transport element 7 and naturally assumes the position of FIG. 4 when advanced. The cutting element 10 also contacts a protrusion 11 on an inner surface 13 of the tubular element 4 which directs the cutting element 10 into the cutting position of FIG. 4. The protrusion 11 may simply be a ring 15 of material attached to the inner surface of the tubular element 4 although any other structure may be used. The transport element 4 and cutting element 10 are then moved proximally to the tissue chamber with the cutting element 10 remaining in the cutting position of FIG. 4 as explained below.

The tissue removal device 2 has a first actuator 24 and a second actuator 26 which are described further below in connection with use of the device 2. When the first actuator 24 is depressed, the introducer 20 is retracted proximally to the position shown in FIG. 6 so that the open end of the tubular element 4 is exposed to receive tissue. When the second actuator 26 is depressed, the tubular element 4 is driven forward so that tissue enters the open end 6. The cutting element 10 is then automatically advanced to part off tissue which has entered the open end 10 and the transport element 7 then transports the tissue to the tissue chamber 30. The first and second actuators 24, 26 may be knobs, buttons, levers or triggers and FIGS. 1 and 2 show the first and second actuators 24, 26 being buttons.

Figure 6:
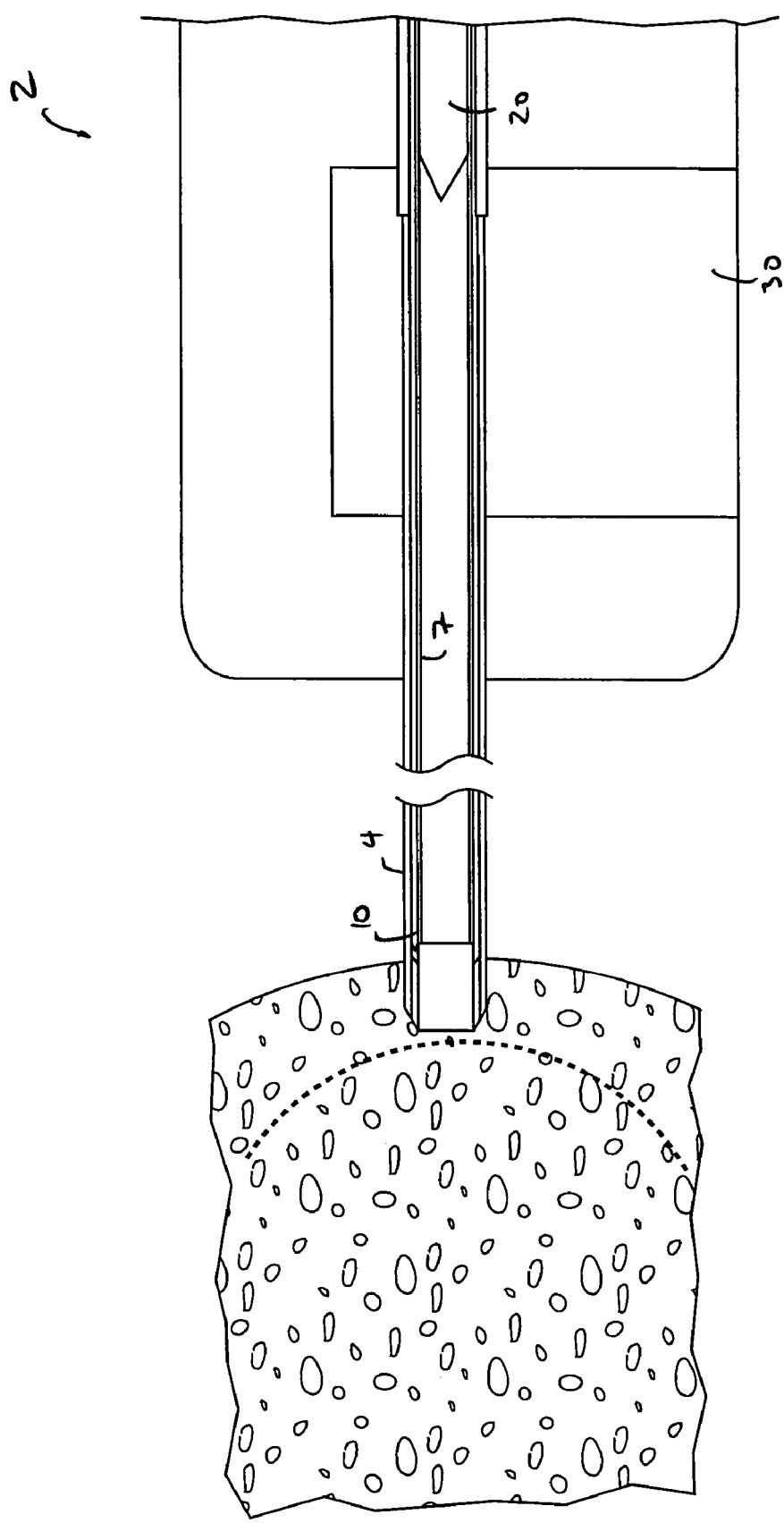
FIG. 6 shows an introducer withdrawn from the distal end.

Use of the tissue removal device 2 is now described in connection with FIGS. 5-11. The device 2 is introduced into the patient for removal of tissue such as breast tissue in a breast biopsy procedure. The device 2 is introduced directly into the tissue with the sharp tip 22 of the introducer 20 penetrating tissue as shown in FIG. 5. The device 2 may also be introduced into the patient through a sheath, trocar or cannula (not shown). Once the distal end is positioned proximal to the tissue to be removed, the first actuator 24 is depressed to withdraw the introducer 20 and expose the open end 6 as shown in FIG. 6. After retracting the introducer 20 the user may, of course, manipulate the device 2 as necessary so that the device 2 is directed toward the tissue to be removed. The introducer 20 may be withdrawn to a position proximal to the tissue chamber 30 or another suitable position.

Figure 7:
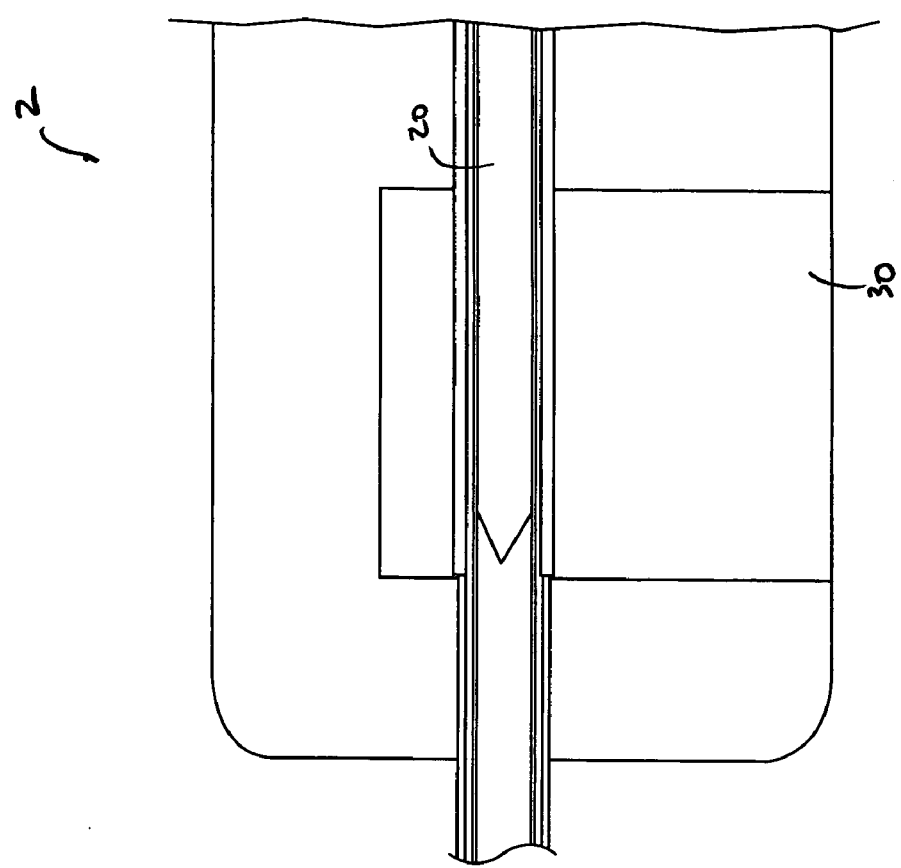
FIG. 7 shows a tubular element advanced into tissue.

The second actuator 26 is then depressed which causes the tubular element 4 to be driven forward so that tissue enters the open end 6 as shown in FIG. 7. The transport element 7 may be advanced with the tubular element 4 or may be driven independently of the tubular element 4 without departing from the invention. For example, the transport element 7 may be driven into the position of FIG. 7 after the tubular element 4 has been driven into the tissue and even after the cutting element 10 has been deployed to the position of FIG. 8. The tubular element 4 may also be rotated while being driven forward, for example, the tubular element 4 may be rotated 0.5 to 3 revolutions when driven forward. The tubular element 4 may also simply be translated (without rotating) without departing from numerous aspects of the present invention. The introducer 20 may be advanced with the tubular element 4 as shown in FIG. 7.

Figure 8:
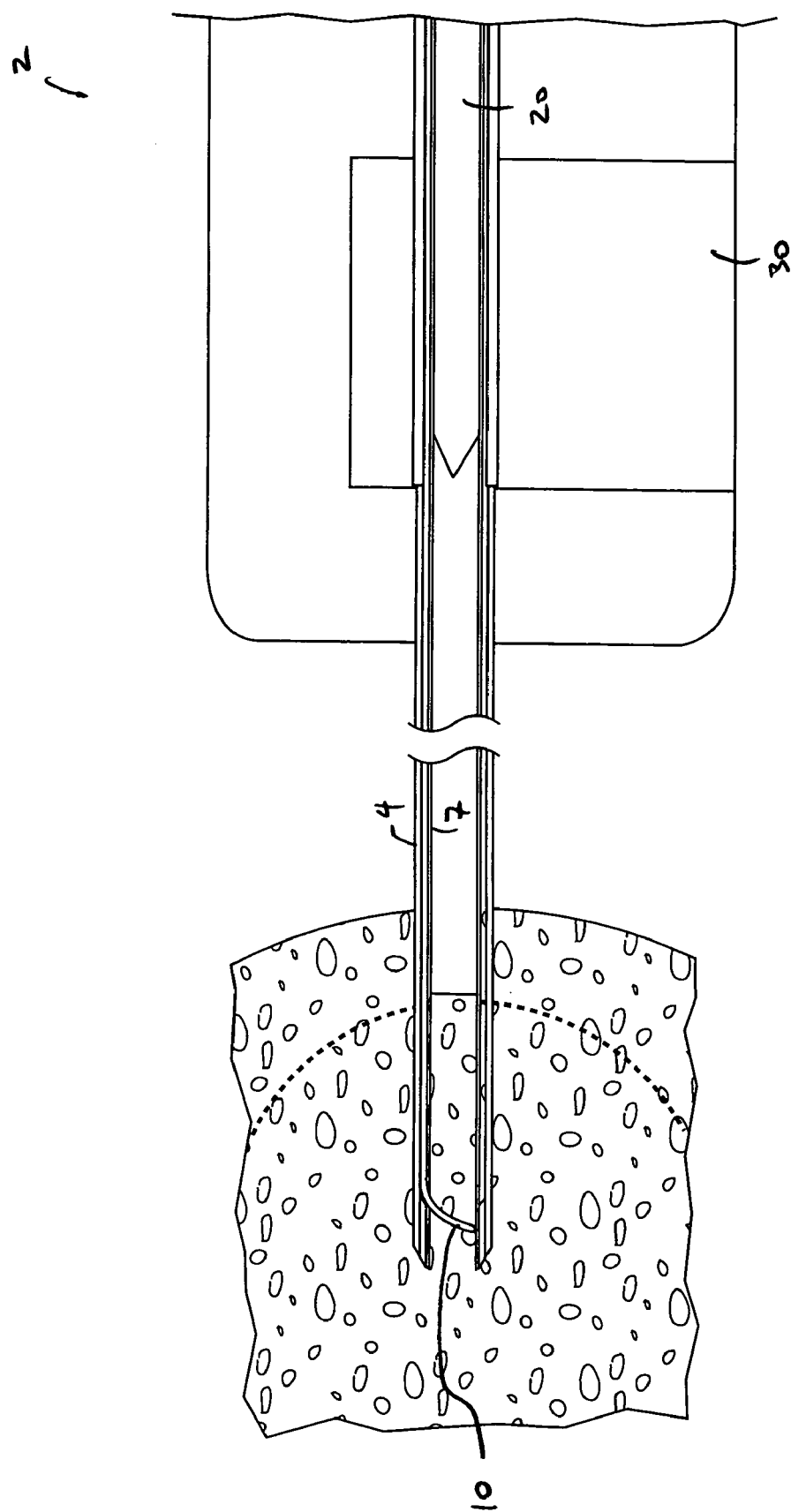
FIG. 8 shows a cutting element cutting tissue which has entered the tubular element.

The cutting element 10 is then advanced until it contacts the protrusion 11 and is directed into the tissue which has entered the tubular element 4 as shown in FIGS. 4 and 8. The cutting element 10 extends toward and through a longitudinal axis defined by the tubular element 4 and forms an angle of about 70 degrees with the longitudinal axis although any other suitable angle may be used. The cutting element 10, transport element 7 and/or tubular element 4 may also be rotated to aid in cutting the tissue. The cutting element 10 may be rotated with the tubular element 4 in the same direction or in opposite directions when parting off the tissue which has entered the device 2.

Figure 9:
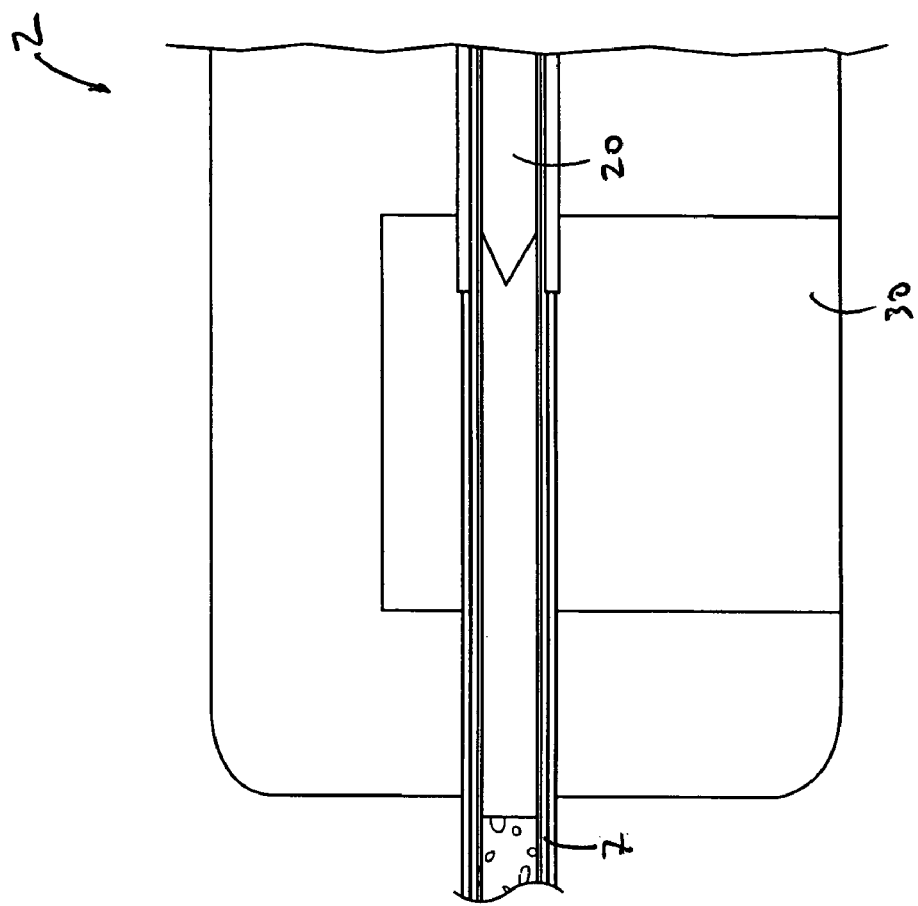
FIG. 9 shows the tissue being transported proximally.

The transport element 7 and cutting element 10 then move proximally toward the tissue chamber 30 as shown in FIG. 9. The introducer 20 is positioned so that continued proximal movement of the transport element 7 brings the tissue into contact with the distal end of the introducer 20 as shown in FIG. 10. Continued proximal movement of the transport element 7 completely exposes the tissue and permits the tissue to fall into the tissue chamber 30 as shown in FIG. 11. The tubular element 4 has an opening 32 leading to the tissue chamber 30 to permit the tissue to fall into the tissue chamber 30 when the tubular element 4 is in the position of FIG. 11.

The cutting element 10 is straightened by withdrawing the cutting element 10 into a recess (not shown). The cutting element 10 and transport element 7 are then moved back to the position of FIG. 6. The tubular element 4 may remain within the patient during transport of the tissue to the tissue chamber 30 so that the device 2 is ready to take another tissue mass without removing the device 2 from the patient. The user may re-orient the device 2 as necessary so that the tubular element 4 is directed at tissue to be removed. The user then actuates the second actuator 26 again which causes the tubular element 4 to be driven forward to collect another tissue mass. If a tissue mass is desired at another location, the user may actuate the first actuator 24 to move the introducer 20 back to the position of FIG. 5. The device 2 may then be manipulated to position the device 2 at the next location where tissue is to be removed.

Figure 12:
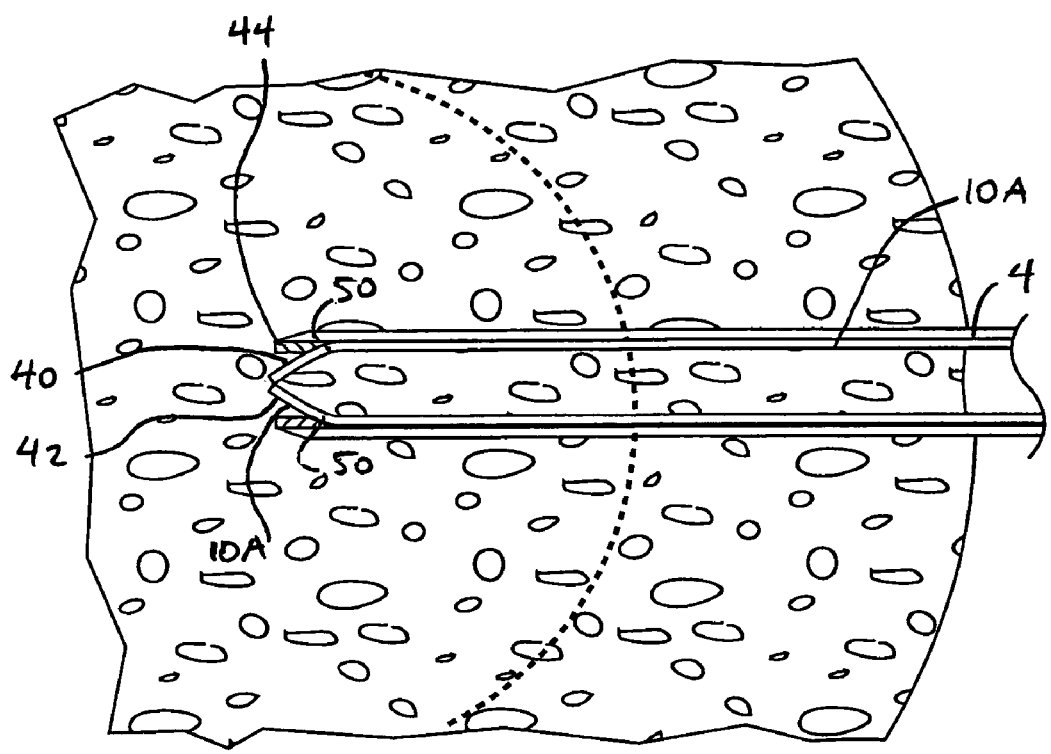
FIG. 12 is a cross-sectional view of another tissue removal device.
Figure 13:
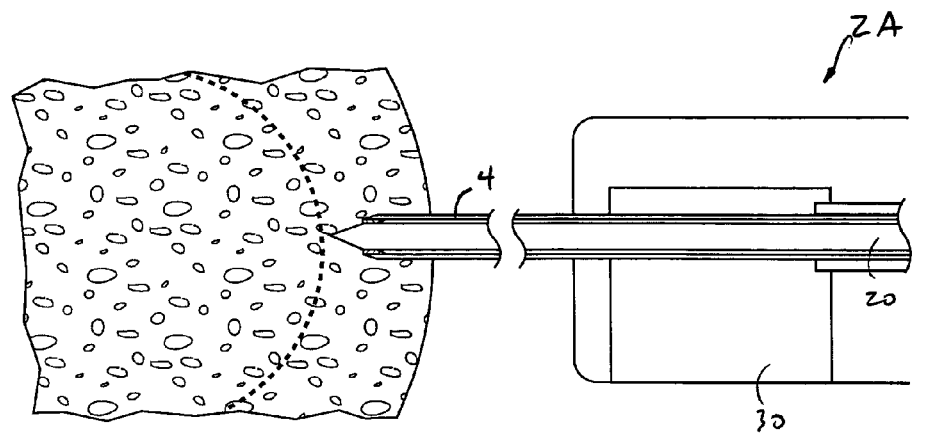
FIG. 13 shows the device of FIG. 12 introduced into tissue.

Referring to FIGS. 12-18, another device 2A for removing tissue is shown wherein the same or similar reference numbers refer to the same or similar structure. The cutting element 10A has a first part 40 and a second part 42 which may be integrally formed or may be independent elements. The first and second parts 40, 42 move inwardly to cut the tissue which has entered the tubular element 4 as shown in FIG. 12. The first and second parts 40, 42 move inwardly when they engage a protrusion 44 on an inner wall 46 of the tubular element 4A as shown in FIG. 12. The protrusion 16 may be a ring 21 which directs the first and second parts 40, 42 inwardly.

The first and second parts 40, 42 may each include a portion 50 which undergoes plastic deformation when moving to the position of FIG. 12. The first and second parts 40, 42 remain in the closed position until they are withdrawn into recesses (not shown) which straighten the two parts 40, 42. The first and second parts 40, 42 may also lock together or may be naturally biased to the position of FIG. 12 rather than being plastically deformed without departing from numerous aspects of the present invention.

The cutting element 10A is used to transport then tissue to the tissue chamber 30 after parting off the tissue. The cutting element 10A moves proximally as shown in FIGS. 17 and 18 to transport the tissue to the tissue chamber 30. The tissue may contact the introducer 20 or another part of the device 2A as the tissue is moved proximally to help release the tissue from the cutting element 10A.

Figure 14:
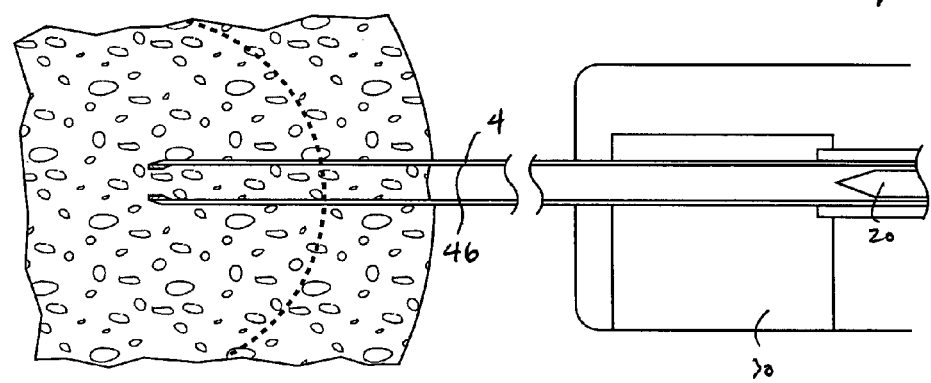
FIG. 14 shows the introducer retracted.
Figure 15:
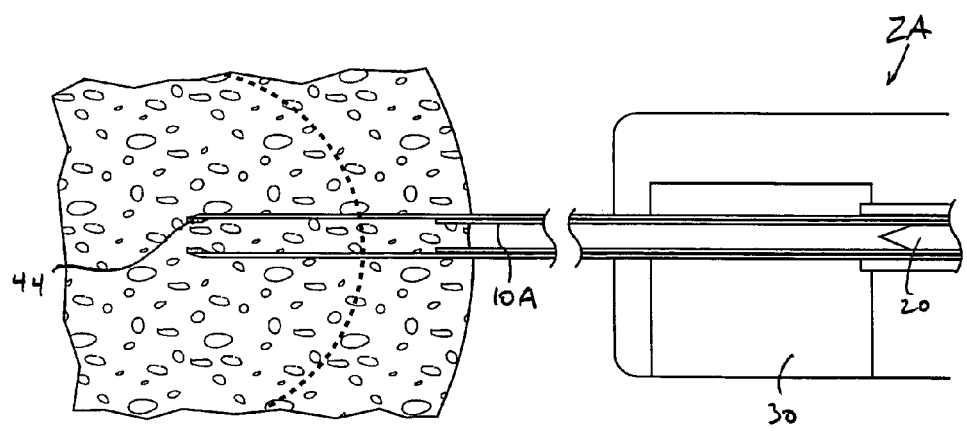
FIG. 15 shows the cutting element being advanced distally.

Use of the device 2A is similar to use of the device 2 described above. The first actuator 24 is depressed to retract the introducer 20 as shown in FIG. 14. The second actuator 26 is then depressed which causes the tubular element 4A to be advanced into tissue as shown in FIG. 14. The cutting element 10A is then advanced to part off the tissue which entered the open end as shown in FIGS. 12 and 16. The cutting element 10A may be moved together with the tubular element 4A when the tubular element 4A is advanced or may be driven over the tissue after the tissue has entered the tubular element 4A. The cutting element 10A then moves proximally toward the tissue chamber 30 as shown in FIG. 17 and deposits the tissue in the tissue chamber 30 as shown in FIG. 18. The first and second parts 40, 42 are opened when they are withdrawn into the recesses (not shown).

The tubular element 4A and cutting element 10 are then moved back into position to take another tissue mass. As such, the tissue removal device 2 does not need to be removed from the patient so that the user may simply reorient the device 2 or move the device 2 to another location where tissue is to be removed as described above. The method described in connection with FIGS. 12-18 may also be accomplished with the device of FIGS. 2-11 in that the cutting element 10 may be used to transport the tissue mass by itself. Such a method and use of the device 2 of FIGS. 1-11 is expressly incorporated here.

Figure 19:
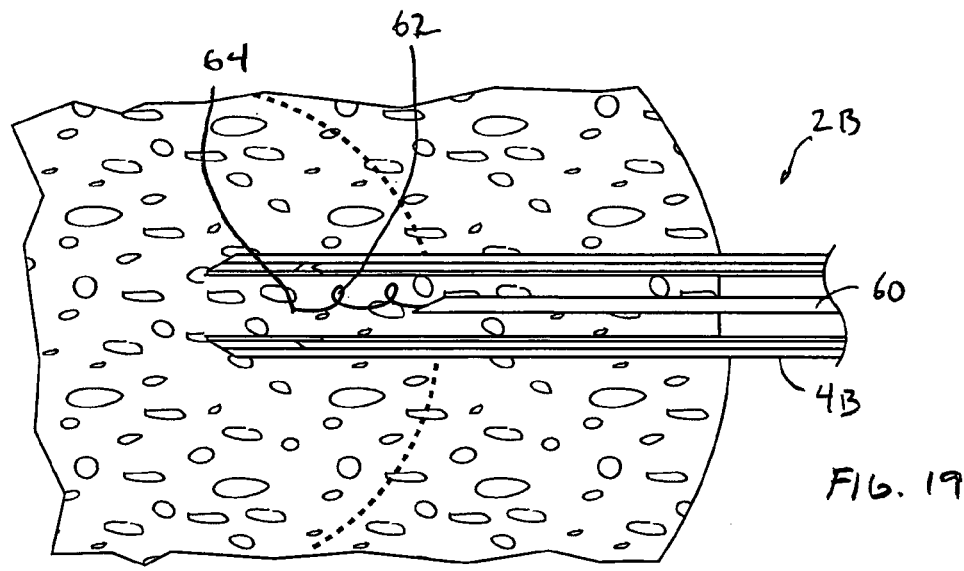
FIG. 19 shows another device for removing tissue from a patient.
Figure 20:
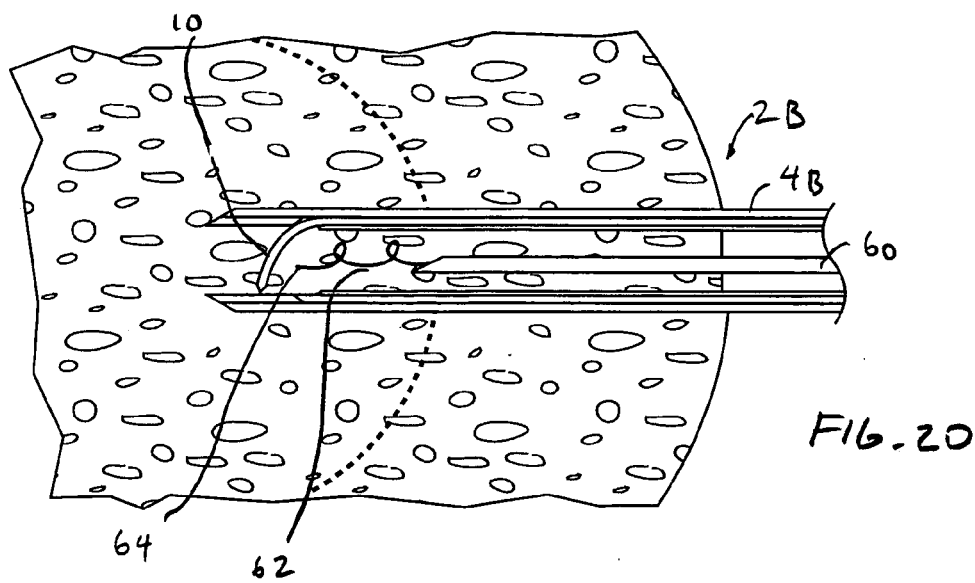
FIG. 20 shows the cutting element cutting the tissue which has entered the tubular element.

Referring to FIGS. 19 and 20, another tissue removal device 2B is shown wherein the same or similar reference numbers refer to the same or similar structure. The tissue removal device 2B has a tubular element 4B which is driven into tissue. The device 2B also has the cutting element 10 which parts off the tissue in the tubular element 4B and the tissue chamber 30 which receives the tissue (see FIGS. 1 and 2). The cutting element 10 and/or tubular element 4B may be rotated to aid in cutting the tissue. The cutting element 10 may be rotated with the tubular element 4 in the same direction or in opposite directions when parting off the tissue which has entered the device 2B. The device 2B also has the first and second actuators 24, 26 which function in the same manner as the first and second actuators 24, 26 described above (also shown in FIGS. 1 and 2).

The device 2B also includes a transport element 60 which moves within the tubular element 4B and engages the tissue. The transport element 60 may be any suitable element which engages and contacts the tissue mass. For example, the transport element 60 may be a wire 62 having a sharp tip 64 which pierces the tissue. The wire 62 may be curved or helical so that the wire 62 may be pivoted or rotated into engagement with the tissue. The transport element 60 may be advanced into the tissue before the tubular element 4B or may be driven into the tissue at the same time as the tubular element 4A or even after the tubular element 4B has been driven into the tissue.

Once the transport element 60 and the tubular element 4A are in the position of FIG. 20, the transport element 60 moves proximally to carry the tissue toward the tissue chamber 30. The transport element 60 may also be rotated in the same direction that was used to engage the tissue when transporting the tissue mass proximally to help maintain engagement with the tissue. The tissue is transported proximally until the tissue contacts the introducer 20 in the manner described above (see FIG. 11). The transport element 60 is then withdrawn thereby permitting the tissue mass to fall into the chamber 30. The transport element 60 may be rotated when being withdrawn from the tissue so that the wire 62 withdraws smoothly from the tissue. The transport element 60, tubular element 4A and cutting element 10 are then moved back into position to take another tissue mass without removing the device 2B from the patient as described above.

Figure 21:
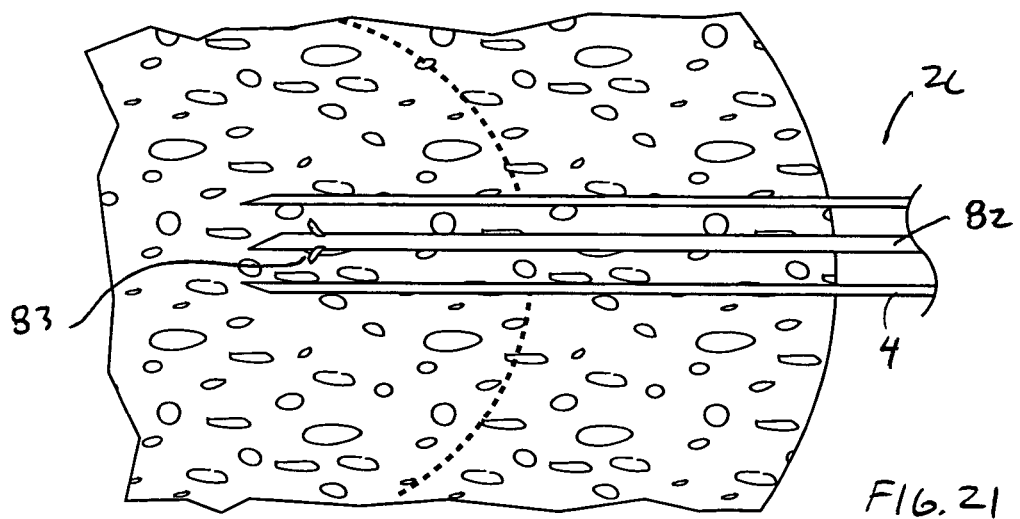
FIG. 21 shows still another device for removing tissue from a patient.
Figure 22:
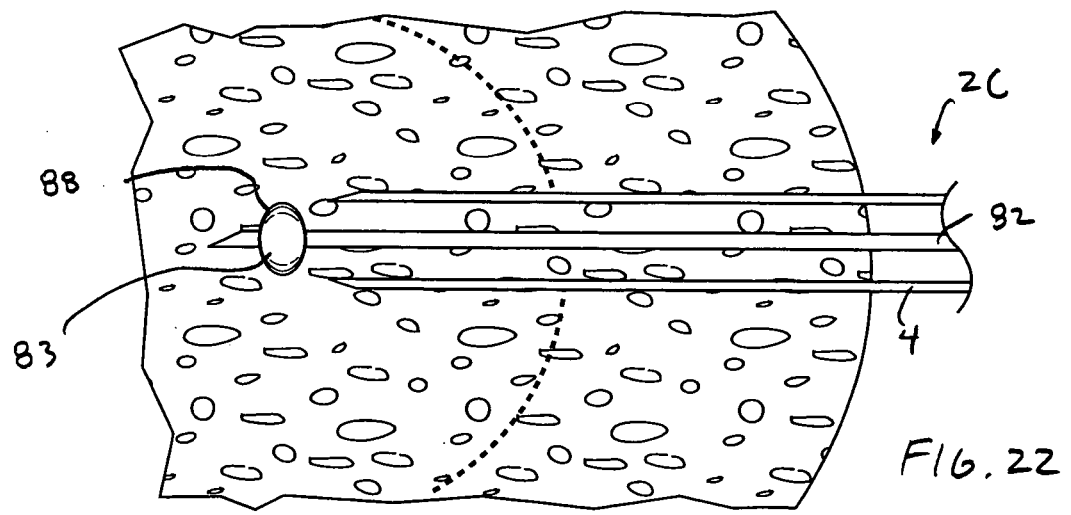
FIG. 22 shows another anchor for the device of FIG. 21.
Figure 23:
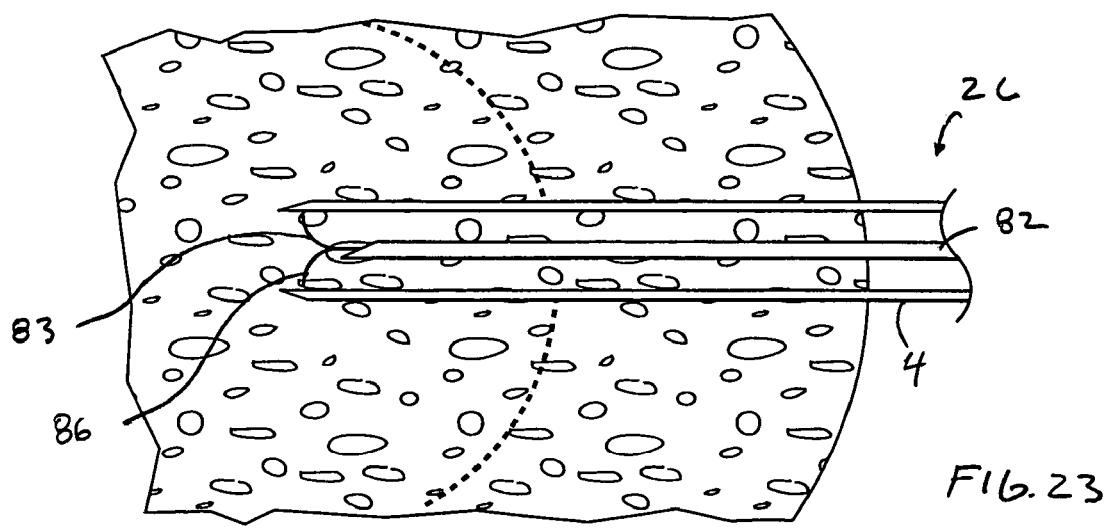
FIG. 23 shows still another anchor for the device of FIG. 21.

Referring to FIG. 21, another tissue removal device 2C is shown wherein the same or similar reference numbers refer to the same or similar structure. The device 2C has a piercing element 82 which pierces the tissue. The piercing element 82 also has a deployable anchor 83 which secures the tissue to the piercing element 82. The anchor 83 may take any suitable form. For example, the anchor 83 may be one or more retractable barbs 84 which hold the tissue as shown in FIG. 21. The barbs 84 may be slightly curved to help hold the tissue on the piercing element 80 but may take any other suitable shape. The anchor 82 may also be one or more wires 86 extending from the piercing element 82 as shown in FIG. 22 or may be an inflatable balloon 88 as shown in FIG. 23.

The device 2C also has the first and second actuators 24, 26 (see FIGS. 1 and 2) which operate in the manner described above. The device also has a third actuator 27 which advances the piercing element 82 when actuated. The piercing element 82 is then moved proximally after the third actuator 27 is actuated again as described below to transport the tissue to the tissue chamber 30.

The device 2C may be operated in a number of different ways including the two now described. In one method, the piercing element 82 is driven into the tissue before the tubular element 4 when the user actuates the third actuator 27. The tubular element 4 is then driven over the piercing element 82 when the user actuates the second actuator 26. The piercing element 82 is then moved proximally to tear the tissue from the surrounding tissue. This step may be performed manually or by actuating the third actuator 27 again. The tissue is then transported proximally by actuating the third actuator 27 again if the user has parted-off the tissue manually.

The piercing element 82 moves proximally until the tissue is over the tissue chamber 30 at which time the anchor 83 is automatically released by withdrawing the barbs 84 or wires 86 or deflating the balloon 88. Further retraction of the piercing element 80 withdraws the piercing element 80 completely thereby permitting the tissue to fall into the tissue chamber 30 as described above in connection with the other devices 2, 2A, 2B. After the tissue has been deposited into the tissue chamber 30, the device 2C is ready to take another sample without removal from the patient as described above.

In another method of operating the device 2C, the tubular element 4 is driven into the tissue first and the piercing element 82 is then driven into the tissue after the tissue has entered the tubular element 4. The anchor 83 is then deployed to secure the tissue to the piercing element 80. The tissue is then separated from the surrounding tissue and transported to the tissue chamber 30 as described above.

The present invention has been described in connection with various preferred embodiments, however, it is understood that various modifications and alternative configurations are possible without departing from the scope of the invention. For example, the piercing element may be adhered to the tissue in any other suitable manner other than using the deployable anchor.

What is claimed is:

1. A method of removing tissue using a coring-type biopsy device having an open end rather than a lateral opening, comprising the steps of:

providing a tissue removal device which is a coring-type device having an open end rather than a lateral opening, the tissue removal device including a tubular element, a transport element, a tissue chamber and a cutting element, the tubular element having an open end at a distal end, the transport element and the cutting element being positioned at least partially within the tubular element and being movable relative to the tubular element, the cutting element being movable relative to the tubular element between a stored position and a cutting position to separate tissue cut by the tubular element from surrounding tissue;

introducing the device into a patient;

advancing the tubular element in a distal direction so that tissue enters the tubular element through the open end, the tubular element being advanced so that tissue also enters the transport element and is positioned within the transport element;

cutting the tissue which has entered the open end by moving the cutting element relative to the tubular element from the stored position to the cutting position after the advancing step, the cutting element separating the tissue which has entered the open end from the surrounding tissue to form a first tissue mass; and transporting the first tissue mass proximally with the transport element to the tissue chamber.

2. The method of removing tissue using a coring-type biopsy device having an open end rather than a lateral opening of claim 1, wherein:
   the providing step is carried out with the transport element also having an open end positioned proximal to the open end of the tubular element; and
   the advancing step is carried out with the tissue entering the transport element through the open end of the transport element.

3. The method of removing tissue using a coring-type biopsy device having an open end rather than a lateral opening of claim 1, wherein:
   the transporting step is carried out with the cutting element being in the cutting position and moving proximally with the transport element when transporting the first tissue mass to the tissue chamber.

4. The method of removing tissue using a coring-type biopsy device having an open end rather than a lateral opening of claim 1, wherein:
   the transporting step is carried out with the distal end of the tubular element remaining within the patient, the distal end of the transport element moving to a position outside the patient when transporting the first tissue mass to the tissue chamber.

5. The method of removing tissue using a coring-type biopsy device having an open end rather than a lateral opening of claim 1, wherein:
   the advancing step is carried out with the cutting element being in the stored position, the cutting element being positioned between the tubular element and the transport element when in the stored position.

6. The method of removing tissue using a coring-type biopsy device having an open end rather than a lateral opening of claim 5, wherein:
   the cutting step is carried out with at least one of the tubular element, the transport element and the cutting element rotating about a longitudinal axis of the tubular element.

7. The method of removing tissue using a coring-type biopsy device having an open end rather than a lateral opening of claim 5, wherein:
   the cutting step is carried out with the cutting element rotating about a longitudinal axis when cutting the tissue.

8. The method of removing tissue using a coring-type biopsy device having an open end rather than a lateral opening of claim 1, further comprising the step of:
   advancing the transport element over the tissue after the tissue has entered the open end of the tubular element.

9. The method of removing tissue using a coring-type biopsy device having an open end rather than a lateral opening of claim 1, further comprising the step of:
   providing an introducer having a sharp tip at a distal end, the tissue chamber being positioned to receive the first tissue mass when the transport element transports the first tissue mass proximally, the introducer being movable between a first position in which the sharp tip extends beyond the open end and a second position in which the sharp tip is positioned away from the open end to expose the open end;
   the introducing step being carried out with the introducer in the first position so that the sharp tip is positioned beyond the open end of the tubular element; and
   the transporting step including the step of contacting the first tissue mass with the distal end of the introducer while the first tissue is transported proximally and when the introducer is in the second position, wherein contact with the distal end of the introducer stops the first tissue mass while the transport element is retracted thereby permitting the first tissue mass to fall into the tissue chamber.

10. The method of removing tissue using a coring-type biopsy device having an open end rather than a lateral opening of claim 1, wherein:
    the cutting and transporting steps are carried out automatically after the advancing step.

\* \* \* \* \*